United States Patent
Stanslaski et al.

(10) Patent No.: US 10,220,204 B2
(45) Date of Patent: Mar. 5, 2019

(54) LEAKAGE DETECTION WITHIN IMPLANTABLE MEDICAL SYSTEM CONDUCTION PATHS

(71) Applicant: MEDTRONIC, INC., Minneapolis, MN (US)

(72) Inventors: Scott R. Stanslaski, Shoreview, MN (US); Timothy R. Abraham, Lino Lakes, MN (US); Timothy J. Denison, Minneapolis, MN (US); Vincent A. Roczniak, Maple Grove, MN (US); Wesley A. Santa, Andover, MN (US); Steven J. Stroncek, Edina, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 17 days.

(21) Appl. No.: 15/665,347

(22) Filed: Jul. 31, 2017

(65) Prior Publication Data

US 2019/0030325 A1 Jan. 31, 2019

(51) Int. Cl.
*A61N 1/08* (2006.01)
*A61N 1/05* (2006.01)
*A61N 1/36* (2006.01)

(52) U.S. Cl.
CPC ............ *A61N 1/08* (2013.01); *A61N 1/0534* (2013.01); *A61N 1/36142* (2013.01); *A61N 1/36164* (2013.01); *A61N 2001/083* (2013.01)

(58) Field of Classification Search
CPC ............ A61N 2001/083; A61N 1/3603; A61N 1/36142
See application file for complete search history.

(56) References Cited

U.S. PATENT DOCUMENTS

| | | | |
|---|---|---|---|
| 5,423,871 A | 6/1995 | Hoegnelid et al. | |
| 5,683,430 A | 11/1997 | Markowitz et al. | |
| 5,755,742 A | 5/1998 | Schuelke et al. | |
| 6,553,260 B1 * | 4/2003 | Skoldengen ....... | A61N 1/37252 607/27 |
| 6,690,974 B2 | 2/2004 | Archer et al. | |

(Continued)

OTHER PUBLICATIONS

Franck et al.: "Averaged Electrode Voltage Testing to Diagnose an Unusual Cochlear Implant Internal Device Failure", Journal of the American Academy of Audiology, vol. 15: 643-648, Nov. 9, 2004.

*Primary Examiner* — Kennedy Schaetzle
(74) *Attorney, Agent, or Firm* — Withers & Keys, LLC

(57) ABSTRACT

Leakage of signal between conduction paths of an implantable medical lead or lead and lead extension combination is detected. A stimulation signal is provided via one electrode. Two other electrodes sense the stimulation signal. A difference in amplitude of the two sensed signals is determined and based on this difference, leakage is detected. A sensing circuit may use differential amplification of the two signals and compare a resulting output signal to a leakage threshold. When the amplitude of the output signal exceeds the leakage threshold, then leakage is occurring between the conduction path providing the stimulation and one of the conduction paths used for sensing. Other techniques for determining leakage from the difference may also be used such as comparing the amplitudes of the two sensed signals and providing a value that is based on the comparison to indicate whether leakage is present.

29 Claims, 5 Drawing Sheets

(56) References Cited

U.S. PATENT DOCUMENTS

| | | |
|---|---|---|
| 6,978,171 B2 | 12/2005 | Goetz et al. |
| 7,047,083 B2 | 5/2006 | Gunderson et al. |
| 7,454,249 B1 | 11/2008 | Bornzin et al. |
| 7,567,840 B2 | 7/2009 | Armstrong |
| 7,574,259 B1 | 8/2009 | Pei et al. |
| 7,623,919 B2 | 11/2009 | Goetz et al. |
| 7,974,690 B2 | 7/2011 | Kracker |
| 8,577,457 B2 | 11/2013 | Miller et al. |
| 8,588,911 B2 | 11/2013 | Nygard et al. |
| 8,750,997 B2 | 6/2014 | Lyden et al. |
| 9,014,807 B2 | 4/2015 | Bocek |
| 9,037,259 B2 | 5/2015 | Mathur |
| 9,238,143 B2 | 1/2016 | Doerr |
| 9,272,150 B2 | 3/2016 | Kroll et al. |
| 2007/0255319 A1* | 11/2007 | Greenberg ............ A61N 1/0543 607/2 |
| 2009/0012372 A1 | 1/2009 | Burnett et al. |
| 2009/0299432 A1* | 12/2009 | Stadler ............... A61N 1/36521 607/28 |
| 2011/0043217 A1 | 2/2011 | Tsampazis et al. |

\* cited by examiner

LEAKAGE DETECTION WITHIN IMPLANTABLE MEDICAL SYSTEM CONDUCTION PATHS

TECHNICAL FIELD

Embodiments provide implantable medical systems, devices, and methods that detect when there is a problem within a conduction path used when providing stimulation therapy. More particularly, embodiments detect when there is leakage between one conduction path and another.

BACKGROUND

Electrical stimulation therapy may be used for various forms of treatment. For example, stimulation therapy may be provided to address neurological issues such as chronic pain, tremors, and the like. In such an example, an implantable stimulation device is typically located in one location of convenience and is connected to electrical leads that are routed to a stimulation site such as within the brain, within the spinal column, within the pelvic region, or elsewhere. The electrical leads include electrodes that interface with the tissue at the stimulation site to deliver the stimulation signals from the stimulation device.

It may be useful to also sense physiological signals nearby the stimulation site. Such signals may be useful to tailor the stimulation therapy to the particular condition being treated and/or to better understand the response of the tissue nearby the stimulation site to the stimulation signals. Sensing physiological signals may be especially useful where the stimulation therapy may be at least partially controlled based on the physiological signals.

In order to provide the stimulation signals and to sense the physiological signals, conduction paths are present within the leads, and in lead extensions when present, in order to carry the signals between the electrodes at the stimulation or sensing site and the implantable medical device that includes the stimulation and sensing circuitry. Each of these conduction paths is formed by one or more fine wires that are insulated relative to the wires of the other conduction paths, where the collection of the one or more fine wires of a given conduction path may be linear or may be coiled along the length of the lead and lead extension. Due to age and patient activity, the insulation separating the conduction paths may deteriorate or may otherwise by damaged. Ingress of bodily fluids may also occur over time. Events such as these may result in signal leakage between conduction paths. Such leakage can result in potentially faulty therapy, particularly due to adverse effects of the leakage when attempting to sense relatively small neurological signals.

To further exacerbate this issue, the impedance of the leakage may be within the range of impedances considered to be normal for the conduction paths. Thus, if an impedance test from one conduction path to another is performed, where one of those conduction paths leaks to the other, then the impedance test will not reveal the leakage. Therefore, therapy may continue to be provided as if no leakage is present, and any issues presented by the leakage will continue to potentially adversely affect the therapy.

SUMMARY

Embodiments may address issues like those above and others by performing leakage detection. One conduction path of the lead, and lead extension when present, that corresponds to a particular electrode is used to provide stimulation which may be at a level below the activation threshold of the surrounding tissue. Two other conduction paths corresponding to two other electrodes are then configured to provide sensing of the stimulation signal. These two sensing conduction paths are connected to the inputs of a sensing circuit that can then determine the extent the amplitude of the two sensed signals differs where an imbalance in magnitude results when leakage is present. For instance, the sensing circuit may include a differential amplifier that receives the signals on the two sensing conduction paths as the inputs. When leakage is present between one of the sensing conduction paths and the stimulation conduction path, the imbalance that occurs on the two sensing paths presents a relatively high differential at the inputs of the differential amplifier. In that case, the differential amplifier produces a sensed signal output having a relatively high amplitude. The amplitude of that sensed signal may be compared to a leakage threshold to indicate that a leakage is present when the leakage threshold is exceeded.

Embodiments provide a method of detecting a signal leakage from a conduction path within an implantable medical lead. The method involves providing a stimulation signal from a first electrode corresponding to a first conduction path of the implantable medical lead. The method further involves sensing the stimulation signal as a first sensed signal via a second electrode corresponding to a second conduction path of the implantable medical device and sensing the stimulation signal as a second sensed signal via a third electrode corresponding to a third conduction paths of the implantable medical lead, with the second and third conduction paths being coupled to a sensing circuit of an implantable medical device. The method further involves detecting whether there is leakage between the first and second conduction paths and/or between the first and third conduction paths based on the difference in amplitude of the first and second sensed signals.

Embodiments provide an implantable medical system that includes an implantable medical device having a stimulation engine, having a sensing circuit and having a controller. The implantable medical system further includes at least one implantable medical lead providing first, second, and third conduction paths. The controller is configured to electrically couple the first conduction path to the stimulation engine to provide a stimulation signal onto the first conduction path, to electrically couple the second and third conduction paths to the sensing circuit where the second conduction path provides a first sensed signal and the third conduction path provides a second sensed signal, and to monitor an output of the sensing circuit to detect whether there is leakage between the first and second conduction paths and/or between the first and third conduction paths based on a difference in amplitude of the first and second sensed signals.

Embodiments provide an implantable medical device that includes a stimulation engine, a sensing circuit, a first, a second, and a third lead connector corresponding to first, second, and third conduction paths, and a controller. The controller is configured to electrically couple the first lead connector to the stimulation engine to provide a stimulation signal onto the first lead connector, to electrically couple the second and third lead connectors to the sensing circuit to produce first and second sensed signals, and to monitor the output of the sensing circuit to detect whether there is leakage between the first and second conduction paths and/or between the first and third conduction paths based on a difference in amplitude of the first and second sensed signals.

DETAILED DESCRIPTION

Embodiments address the potential for undiscovered signal leakage in implantable medical leads and lead extensions by performing a leakage detection procedure. Stimulation, which may be at a level below the threshold for tissue activation, is provided via one conduction path of the lead, and extension when present, while sensing of that stimulation signal is performed via two other conduction paths of the lead, and extension when present. The sensing conduction paths direct the sensed signal to a sensing circuit that can detect the leakage from the difference in amplitude of the sensed signals. For instance, the sensing circuit may include a differential amplifier where both conduction paths that are sensing the stimulation signal are connected to the respective inputs of the differential amplifier so that the output of the amplifier is relatively large when a leakage is present that creates an imbalance on the two sensing conduction paths. The amplitude of the output signal may be compared to a leakage threshold to then determine that there is leakage present when the amplitude exceeds the threshold. As another example, the sensed signals may be compared with a comparator circuit to indicate that one signal exceeds the other by at least a leakage threshold amount.

Figure 1:
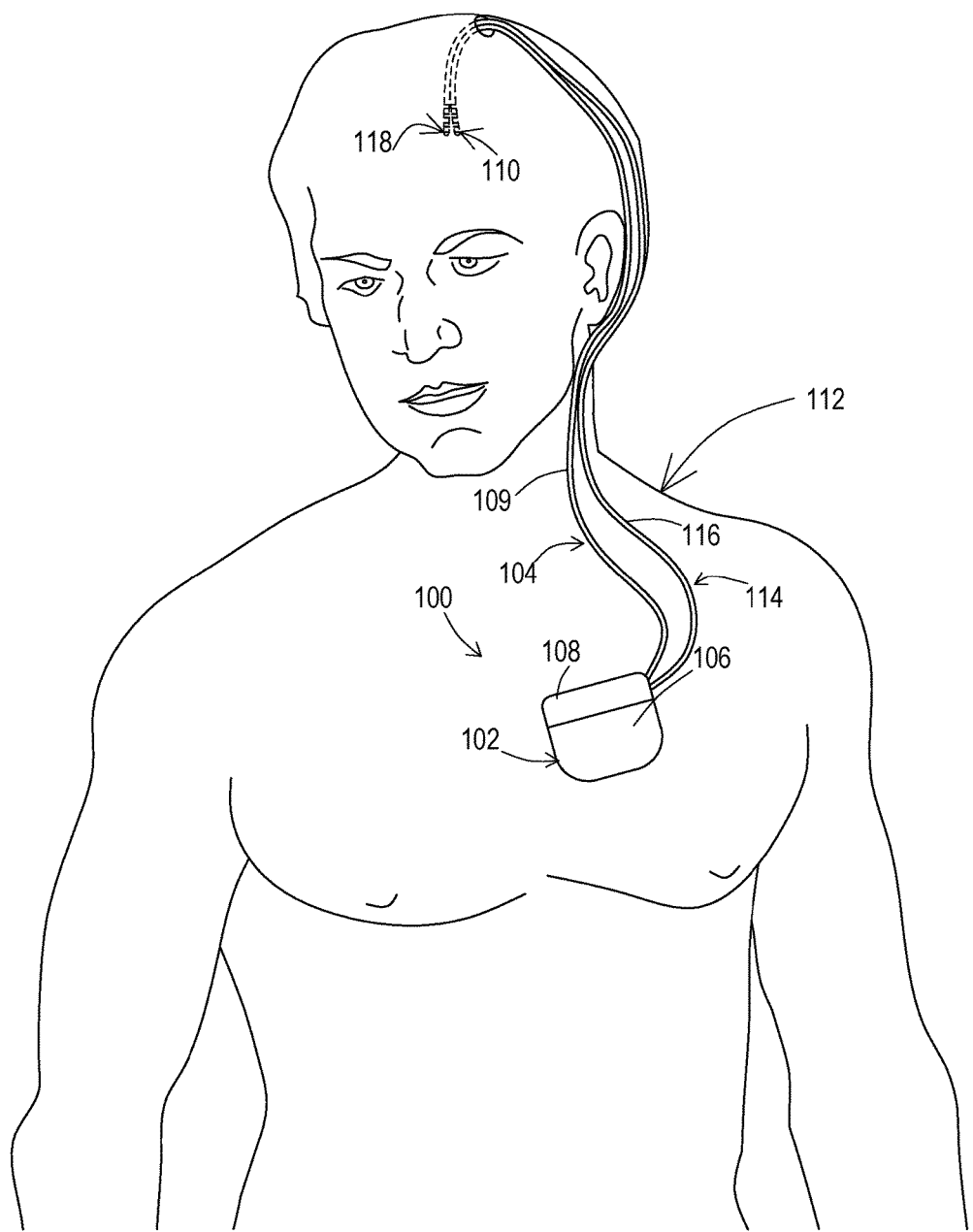
FIG. 1 shows a patient having an example of an implantable medical system for detecting leakage of a conduction path according to various embodiments.

FIG. 1 shows an example of an operating environment for the various embodiments. An implantable medical system 100 is implanted within a body of a patient 112. The implantable medical system 100 includes a stimulation and sensing device 102 coupled to one or more implantable leads 104, 114 or lead and lead extension combinations. The stimulation and sensing device 102 of this example includes a conductive outer casing 106 as well as a header 108 that includes one or more bores where a proximal end of each of the leads or lead extensions 104, 114 is positioned. Each lead or lead and lead extension combination 104, 114 includes a body 109, 116 and a set of one or more electrodes 110, 118 on a distal end of the body 109, 116 which is positioned at a stimulation site within the body of the patient 112. The stimulation and sensing device 102 produces stimulation signals that are delivered through one or more of the conduction paths of the lead 104 and/or lead 114 to the electrodes 110 and/or electrodes 118 where those stimulation signals enter the tissue of the patient 112. The conductive outer casing 106 may be interconnected to the stimulation circuitry and used as an electrode to further provide a conduction path for the stimulation signals.

Likewise, the stimulation and sensing device 102 may sense signals using one or more of the electrodes 110 and/or electrodes 118 via one or more conduction paths within the lead 104 and/or lead 114. During typical therapy, the stimulation and sensing device 102 provides stimulation pulses at a level that exceeds the tissue activation threshold and then between stimulation pulses senses physiological signals emanating from the stimulation site as a result of those stimulation pulses. However, for leakage detection the stimulation signal is provided at an amplitude below the tissue activation threshold via one particular conduction path and corresponding electrode at a time while sensing is simultaneously performed via two other conduction paths and corresponding electrodes.

In one example of therapy, lead 104 may be dedicated to providing the stimulation signal conduction paths while the lead 114 is dedicated to sensing the physiological signal. Alternatively, the same one or more leads may be used to provide both the stimulation and the sensing function during therapy. During leakage detection mode, the same lead 104 or 114 may be used to provide the conduction path and corresponding electrode for the stimulation signal as well as the two conduction paths and corresponding electrodes for sensing the stimulation signal. This is the most likely situation where leakage will be found due to the close proximity of the sensing conduction paths to the stimulation conduction path within the same lead body. However, during leakage detection mode, one lead may also provide the stimulation from a conduction path while sensing is done via conduction paths of another lead, or one lead may provide stimulation through a conduction path while sensing is done with one conduction path of that same lead and with another conduction path of the other lead.

The one or more leads 104, 114, and lead extensions when present, may be of various types. In one example, a lead having a simple electrode array geometry may be used for stimulation and/or for sensing. An example of a simple electrode array geometry may include one or more ring electrodes distributed at different axial positions along the length of a lead. Another example of a simple electrode array geometry is a planar array of electrodes on a paddle lead such as for spinal stimulation sites.

In another embodiment, the one or more leads may have a complex electrode array geometry. A complex electrode array geometry generally refers to an arrangement of stimulation electrodes at multiple non-planar or non-coaxial positions, in contrast to simple electrode array geometries in which the electrodes share a common plane or a common axis. An example of a complex electrode array geometry, in accordance with this disclosure, is an array of electrodes positioned at different axial positions along the length of a lead, as well as at different angular positions about the periphery, e.g., circumference, of the lead. In some embodiments, the electrodes in the complex array geometry may appear similar to non-contiguous, arc-like segments of a conventional ring electrode. A lead with a complex electrode array geometry may include multiple "rings" of such electrode segments. Each ring is disposed at a different axial position. Each electrode segment within a given ring is disposed at a different angular position. The lead may be cylindrical or have a circular cross-section of varying diameter. Such a lead may be referred to as a "segmented" lead.

Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section, particularly for spinal stimulation sites. Examples of complex array geometries are shown and described in U.S. Pat. No. 7,822, 483 entitled "Electrical and Activation Field Models for Configuring Stimulation Therapy" which is assigned to the assignee of the present application and which is incorporated herein by reference. Other types of sensing and/or stimulation electrodes may be used according to the current disclosure, including conformable electrodes, cuff electrodes, segmented electrodes, or any other type of electrodes capable of forming unipolar, bipolar or multi-polar electrode configurations.

The sub-tissue-activation threshold stimulation signals of the leakage detection mode may be delivered using various electrode arrangements such as unipolar arrangements, bipolar arrangements or multipolar arrangements. A unipolar stimulation arrangement generally refers to the use of an anode on the conductive outer casing 106 that sources current and one or more cathodes on one or more leads (e.g., 104, 114) that sink current. A bipolar stimulation arrangement generally refers to the use of an anode on a lead (e.g., lead 104) that sources current and a cathode on the same lead and/or another lead that sinks current. A multipolar stimulation arrangement generally refers to the use of more than one anode on a lead (e.g., lead 104) that each source current and one or more cathodes on the same lead or another lead that sink current, or the use of one anode on a lead that sources current and multiple cathodes on the same lead or another lead that sink current.

A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver the sub-tissue-activation threshold electrical stimulation in accordance with techniques described in this disclosure. However, the example of FIGS. 3 and 4 utilizes unipolar stimulation.

Figure 2:
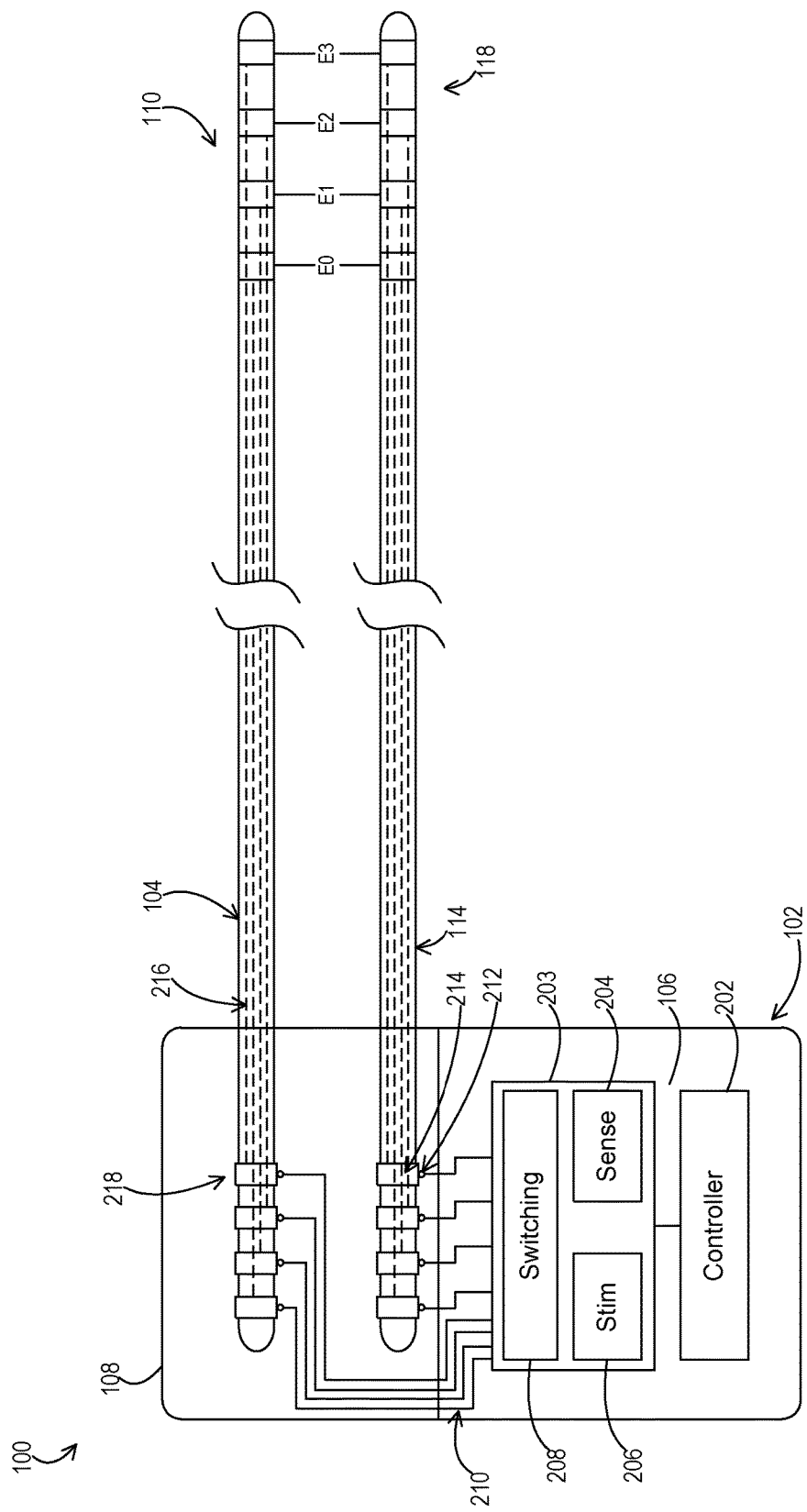
FIG. 2 shows an implantable medical system including a medical device attached to a stimulation lead and a sensing lead or to a sensing and stimulation lead.

FIG. 2 shows an example of the implantable medical system 100 in more detail. Here, the stimulation device 102 includes circuitry 203 including a stimulation engine 206, a sensing circuit 204, and switching module 208. The stimulation device 102 also includes a controller 202 that controls the components 204, 206, and 208 of circuitry 203. During the leakage detection mode, the stimulation engine 206 produces the stimulation pulses that are then applied to the desired conduction path. The switching module 208 interconnects the stimulation engine with the corresponding header conductors 210 and lead connectors 212 of the desired leads 104 or 114 present within the header block 108. The sensing circuit 204 senses the stimulation signal over two desired conduction paths. The switching module 208 interconnects the sensing circuit inputs with the corresponding header conductors 210 and lead connectors 212, of the desired leads 104 or 114.

The controller 202 may be of various forms. For instance, the controller 202 may comprise a general purpose programmable processor that implements programming instructions to bring about the operation of the stimulation engine 206, the sensing circuit 204, and the switching module 208. As other examples, the controller 202 may comprise a dedicated purpose processor and/or hardwired digital logic.

Within the leads or lead and lead extension combinations 104, 114, there are conduction paths 216 where the leakage may occur. These conduction paths electrically interconnect proximal contacts 214, 218 on a proximal end of the leads or lead extensions 104, 114 that is positioned within the header 108 to respective distal electrodes (e.g., E0, E1, E2, and E3) of the electrode sets 110, 118. The proximal contacts 214, 218 are in electrical engagement with the lead connectors 212 so that the stimulation signals and/or sensed signals are passed between the header conductors 210 and lead connectors 212. Thus, the header conductors 210 and lead connectors 212 also form a portion of the conduction paths between the circuitry 203 and the electrode sets 110, 118.

Figure 3:
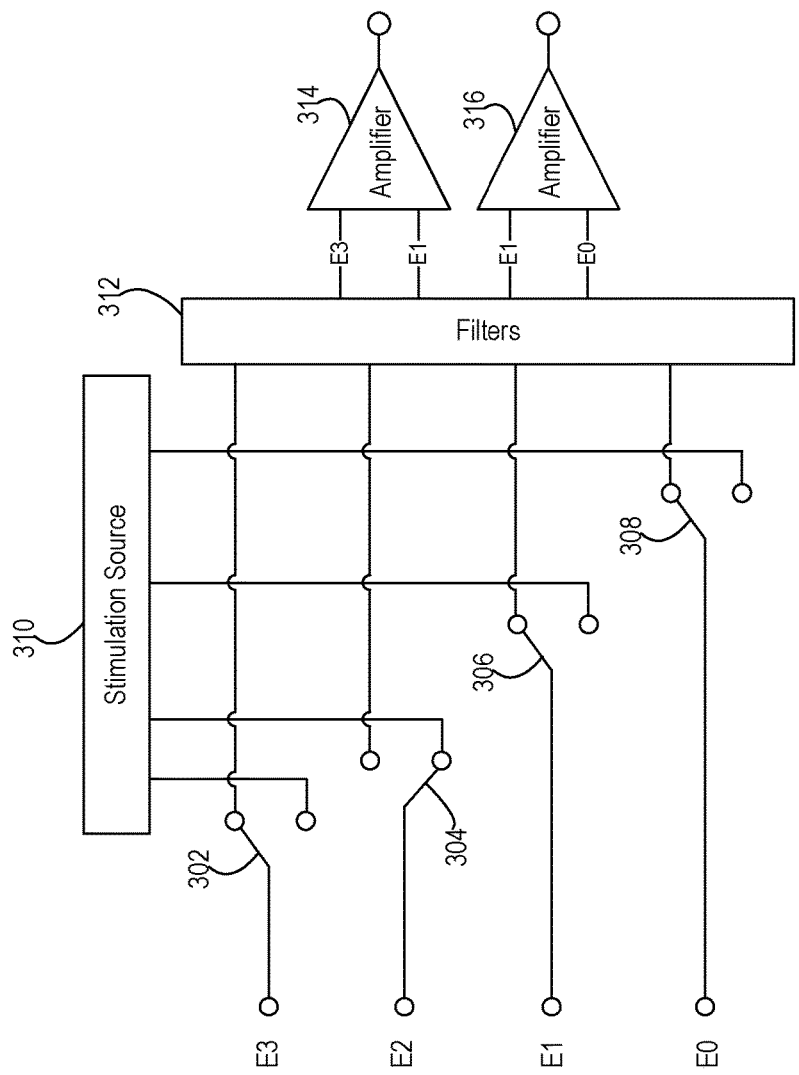
FIG. 3 shows an example of a switching configuration between conduction paths and stimulation and sensing circuitry of a medical device that implements leakage detection for each of the conduction paths.

FIG. 3 shows an example of a configuration of switches 302, 304, 306, and 308, such as those within the switching module 208 of FIG. 2. These switches selectively interconnect a stimulation source 310, such as the output of the stimulation engine 206 of FIG. 2, to the conduction paths 216 of FIG. 2 and the corresponding electrodes E0, E1, E2, and E3. In this example, these switches also selectively interconnect a collection of filters 312 and differential amplifiers 314, 316 of the sensing circuitry 204 to the conduction paths 216 of FIG. 2 and the corresponding electrodes E0, E1, E2, and E3. The configuration shown in FIG. 3 may be duplicated for each lead 104, 114.

The filters 312 may include both high pass and low pass filters that remove extraneous frequencies from the sensed signal on a given conduction path. The filters 312 may include a high pass filter to decouple the conduction path from DC which can occur during blanking periods used during normal therapy mode of operation. The filters 312 may include a low pass filter to avoid waveform spread and to avoid a rectification effect from high frequency interferences that may also occur during normal therapy mode.

During normal therapy mode and during leakage detection mode of this example, the filtered signals are provided as input to the differential amplifiers 314, 316 that scale the amplitude of the differential of the sensed signals as desired to produce the sensed signal output. In leakage detection mode, the differential amplifier 314 is particularly useful for revealing the imbalance between the two input sensed signals that results when leakage between conduction paths is present. As discussed above, during leakage detection mode when the stimulation signal is output at an amplitude below the tissue activation threshold, the output of the differential amplifier is relatively high when leakage is present as compared to when leakage is not present. Therefore, the amplitude of the output of the differential amplifier receiving sensed signals where leakage is present may be relied upon during leakage detection mode to ultimately determine whether leakage is occurring.

Each of the switches 302, 304, 306, and 308 may be implemented in silicon or in other manners. In this example, each switch has multiple states where a first state interconnects to the stimulation source 310 of the stimulation engine 206 and a second state interconnects to the filters 312 of the sensing circuitry 204. The switches may include a third state that connects to neither the stimulation source 310 nor the filters 312 to allow the conduction path and corresponding electrode to electrically float or may allow the conduction path to be interconnected to system ground.

In the example shown, this particular stage of the leakage detection mode configures the switches such that switch 304 allows the stimulation signal to be provided via E2. It is further noted that no other electrode carries the stimulation signal in this example, but unipolar stimulation is used instead by relying on the outer casing 106 as shown in FIGS. 1 and 2 to serve as the other stimulation electrode. Switches 302 and 306 allow the electrodes E3 and E1 and corresponding conduction paths to carry sensed signals to associated filters 312 and ultimately to the differential amplifier 314. Switches 306 and 308 allow the electrodes E1 and E0 and corresponding conduction paths to carry sensed signals to associated filters 312 and ultimately to the differential amplifier 316. By using two sensing channels as shown, corresponding to the amplifier 314 and the amplifier 316, all sensing electrodes and conduction paths may be simultaneously active even where a given electrode (e.g., E1 as in this example) provides a sensed signal to both channels. An alternative may use a single sensing channel, such as amplifier 314, and sense with one pairing of sensing electrodes first and then subsequently sense with the other pairing of sensing electrodes. As discussed below with respect to FIG. 4, the leakage mode of operation may cycle through various combinations of electrodes for stimulation and for sensing to ultimately test each conduction path for potential leakage to each of the other conduction paths.

While in this example of FIG. 3, the differential amplifiers 314, 316 that are already used for the therapy mode may also be used for the leakage detection mode, other circuitry may be used instead to detect the difference in the amplitude of the sensed signals in order to detect that leakage is present. For instance, the amplitudes of the two sensed signals may instead be compared with a comparator circuit to detect whether the amplitudes differ by an amount meeting a leakage threshold. The output of the comparator circuit may then output one value indicating no leakage is present when the difference in amplitudes does not exceed the leakage threshold or may output another value indicating that leakage is present when the difference in amplitudes does exceed the leakage threshold.

Figure 4:
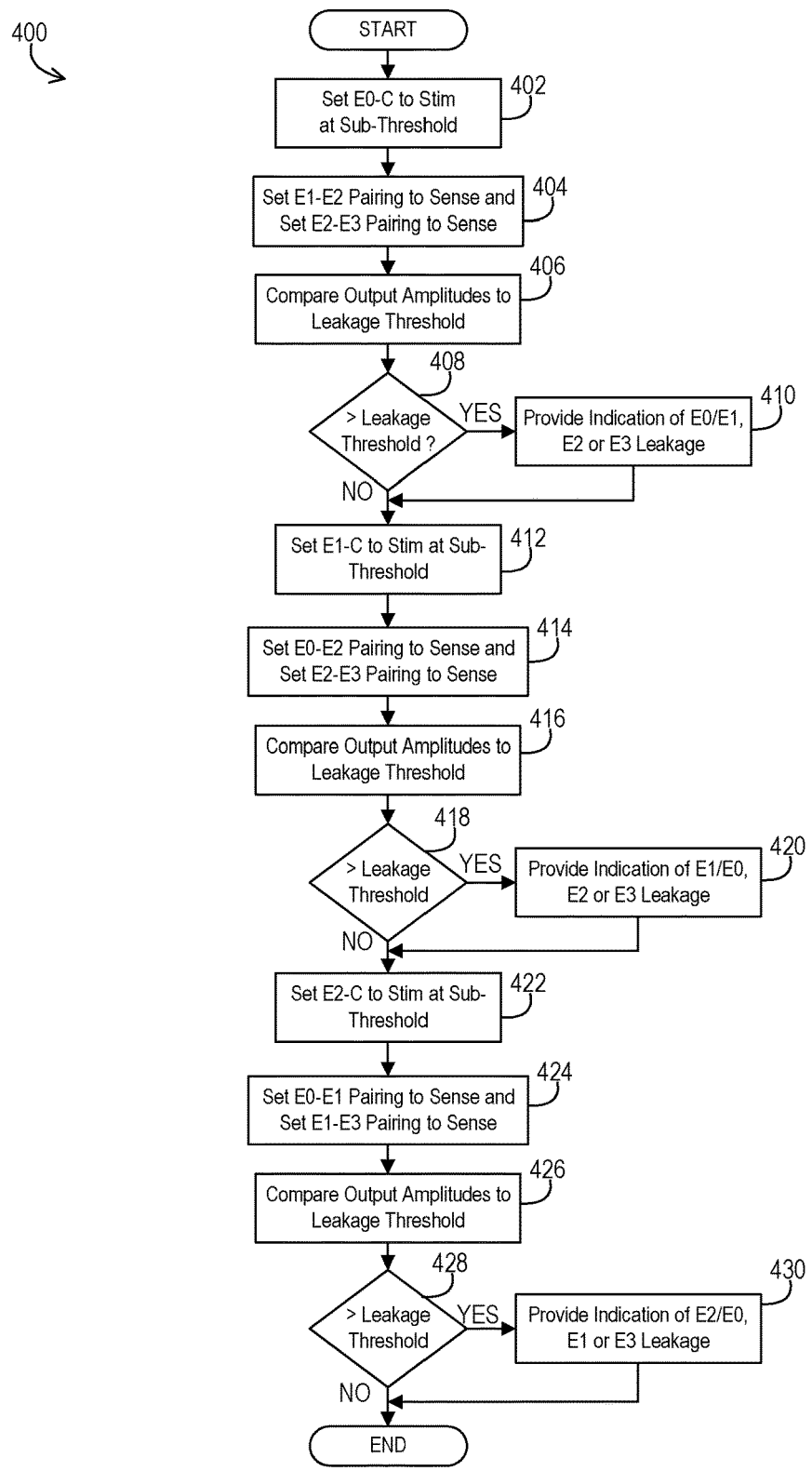
FIG. 4 shows an example of logical operations that may be performed to implement the leakage detection.

An example 400 of logical operations that establish the leakage detection mode of the implantable medical device 102 is shown in FIG. 4. The implantable medical device 102 may autonomously and periodically switch from the normal therapy mode to the leakage detection mode and then return to normal therapy mode immediately thereafter. Alternatively, the implantable medical device 102 may implement the leakage detection mode upon being programmed into the mode by an external programmer device.

In the example of FIG. 4, the operations begin by the controller 202 establishing a first test configuration by setting the switch 308 to connect E0 and the corresponding conduction path to carry stimulation at the amplitude below the tissue activation threshold at an operation 402. The controller 202 also sets the switch 306 and the switch 304 to connect E1 and E2, respectively, and the corresponding conduction paths to carry sensed signals at an operation 404. In this example, the outer casing 106 acts as the stimulation electrode to establish unipolar stimulation. When using multiple sensing channels, then switch 302 may also connect E3 to the appropriate sensing channel paired with E2. The sensed signal for E1-E2 is acquired while the sensed signal for E2-E3 is acquired. If using a single sensing channel and sequential sensing instead, then once the sensed signal has been captured via E1 and E2 while E3 floats or is otherwise unused, then the controller 202 establishes a second test configuration. This second test configuration sets the switch 302 to place E3 in the sensing position and the switch 306 to place E1 in the floating or otherwise unused position at the operation 404 while the stimulation signal is again captured but via E2 and E3.

In either approach, at this point, there is information available to determine if there is a leak between the E0 and the E1, E2, or E3 conduction paths. In examples where a differential amplifier is used for the sensing channel, the controller compares the sensed output signal amplitude of the differential amplifier for a given channel to the threshold at an operation 406. In examples where a comparator circuit is used, the comparator determines whether the difference exceeds a leakage threshold and outputs a fixed value one way or the other. Query operation 408 detects whether the sensed output signals of the amplifiers exceeds a leakage threshold level to signify leakage is present. In the alternative where a comparator circuit is used, then query operation 408 detects whether the comparator circuit output is a value signifying leakage. For one sensing pairing, it may be discovered that leakage is present either between E0 and E1 conduction paths or between E0 and E2 conduction paths. For the other sensing pairing, it may be discovered that leakage is present either between E0 and E2 conduction paths or between E0 and E3 conduction paths. If there is leakage as determined at query operation 408, then the implantable medical device 102 may provide an indication of the leakage at an operation 410 such as by providing information to an external programmer via telemetry. Alternatively, the external device itself may gather the sensed signal outputs or comparator circuit outputs to perform the comparison and leakage detection itself from that information.

To continue looking at other possible leakage paths, the controller switches to a different electrode for providing the stimulation. The controller may establish a third test configuration by setting the switch 306 to connect E1 and the corresponding conduction path to carry stimulation at the amplitude below the tissue activation threshold at an operation 412. The controller 202 also sets the switch 308 and the switch 304 to connect E0 and E2, respectively, and the corresponding conduction paths to carry sensed signals at an operation 414. In this example, the outer casing 106 again acts as the stimulation electrode to establish unipolar stimulation. When using multiple sensing channels, then switch 302 may also connect E3 to the appropriate sensing channel paired with E2. The sensed signal for E0-E2 is acquired while the sensed signal for E2-E3 is acquired. If using a single sensing channel and sequential sensing instead, then once the sensed signal has been captured via E0 and E2 while E3 floats or is otherwise unused, then the controller 202 establishes a fourth test configuration. This fourth test configuration sets the switch 302 to place E3 in the sensing position and the switch 308 to place E0 in the floating or otherwise unused position at the operation 414 while the stimulation signal is again captured but via E2 and E3.

In either approach, at this point, there is information available to determine if there is a leak between the E1 and the E0, E2, or E3 conduction paths. In examples where a differential amplifier is used for the sensing channel, the controller compares the sensed output signal amplitude of the differential amplifier for a given channel to the threshold at an operation 416. In examples where a comparator circuit is used, the comparator determines whether the difference exceeds a leakage threshold and outputs a fixed value one way or the other. Query operation 418 detects whether the sensed output signals of the amplifiers exceeds a leakage threshold level to signify leakage is present. In the alternative where a comparator circuit is used, then query operation 418 detects whether the comparator circuit output is a value signifying leakage. For one sensing pairing, it may be discovered that leakage is present either between E1 and E0 conduction paths or between E1 and E2 conduction paths. For the other sensing pairing, it may be discovered that leakage is present either between E1 and E2 conduction paths or between E1 and E3 conduction paths. If there is leakage as determined at query operation 418, then the implantable medical device 102 may provide an indication of the leakage at an operation 420 such as by providing information to an external programmer via telemetry. Alternatively, the external device itself may gather the sensed signal outputs or comparator circuit outputs to perform the comparison and leakage detection itself from that information.

To again continue looking at other possible leakage paths, the controller switches to another different electrode for providing the stimulation. The controller may establish a fifth test configuration by setting the switch 304 to connect E2 and the corresponding conduction path to carry stimulation at the amplitude below the tissue activation threshold at an operation 422. The controller 202 also sets the switch 308 and the switch 306 to connect E0 and E1, respectively, and the corresponding conduction paths to carry sensed signals at an operation 424. In this example, the outer casing 106 again acts as the stimulation electrode to establish unipolar stimulation. When using multiple sensing channels, then switch 302 may also connect E3 to the appropriate sensing channel paired with E1. Note that this is the configuration demonstrated in FIG. 3. The sensed signal for E0-E1 is acquired while the sensed signal for E1-E3 is acquired. If using a single sensing channel and sequential sensing instead, then once the sensed signal has been captured via E0 and E1 while E3 floats or is otherwise unused, then the controller 202 establishes a sixth test configuration. This sixth test configuration sets the switch 302 to place E3 in the sensing position and the switch 308 to place E0 in the floating or otherwise unused position at the operation 424 while the stimulation signal is again captured but via E1 and E3.

In either approach, at this point, there is information available to determine if there is a leak between the E2 and the E0, E1, or E3 conduction paths. In examples where a differential amplifier is used for the sensing channel, the controller compares the sensed output signal amplitude of the differential amplifier for a given channel to the threshold at an operation 426. In examples where a comparator circuit is used, the comparator determines whether the difference exceeds a leakage threshold and outputs a fixed value one way or the other. Query operation 428 detects whether the sensed output signals of the amplifiers exceeds a leakage threshold level to signify leakage is present. In the alternative where a comparator circuit is used, then query operation 428 detects whether the comparator circuit output is a value signifying leakage. For one sensing pairing, it may be discovered that leakage is present either between E2 and E0 conduction paths or between E2 and E1 conduction paths. For the other sensing pairing, it may be discovered that leakage is present either between E2 and E1 conduction paths or between E2 and E3 conduction paths. If there is leakage as determined at query operation 428, then the implantable medical device 102 may provide an indication of the leakage at an operation 430 such as by providing information to an external programmer via telemetry. Alternatively, the external device itself may gather the sensed signal outputs or comparator circuit outputs to perform the comparison and leakage detection itself from that information.

At this point, the leakage detection mode may end. It will be appreciated that even though E3 is not used to provide stimulation during the leakage detection mode of this example, any leakage involving E3 will be detected by at least one of the test configurations where E3 is involved in the sensing. Therefore, performing other test configurations where E3 is configured as a stimulation conduction path is unnecessary and redundant. While this particular example in FIG. 4 utilizes the specific electrodes E0, E1, and E2 for stimulation in the various configurations while utilizing E3 only for sensing, it will be appreciated that a different combination of electrodes could be used for stimulation while a different electrode may be used only for sensing during leakage detection mode. For instance, E1, E2, and E3 could be used for stimulation in various configurations while E0 is only used for sensing.

Once the leakage detection has ended, then normal therapy mode may resume. However, to the extent the leakage detection mode finds that leakage is occurring, then the normal therapy mode may be adapted as necessary. For instance, if leakage involving a conduction path used for sensing during normal therapy mode occurs, then sensing using that conduction path may be terminated. As another example, if any leakage is found, then sensing may be terminated for all conduction paths of the lead.

Figure 5:
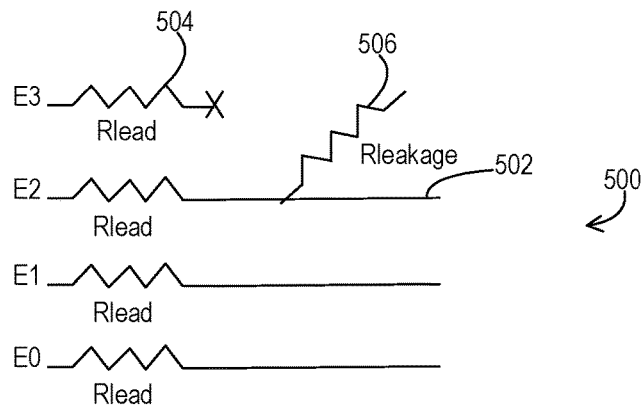
FIG. 5 shows a circuit that models a leakage scenario that is being detected.

FIG. 5 shows a circuit model 500 of a particular leak scenario. In this example, each conduction path has an impedance referred to as Rlead. When implanted, Rlead includes the tissue interface impedance such that the Rlead is in the range of up to a few kilo-ohms at typical stimulation frequencies. While the circuit model 500 represents this impedance as a resistor 504 for each conduction path, it will be appreciated that the impedance is actually complex and not merely a resistance at stimulation frequencies.

In this scenario of FIG. 5, the conduction path of E3 leaks to the conduction path 502 of E2, where a leakage path 506 from the E3 conduction path to conduction path 502 has an impedance referred to as Rleakage that is typically greater than the Rlead 504 of E3. However, Rleakage may only be larger by a small factor so that when measuring impedance from E3 to E2, the total impedance looks to be within the normal range. However, using the leakage mode discussed above, when E2 is used for stimulation and sensing is set to utilize E3 and E1, there will be an imbalance due to Rleakage producing a different signal amplitude than Rlead on the conduction path of E1. This imbalance is then detected in order to indicate that leakage is present.

Figure 6:
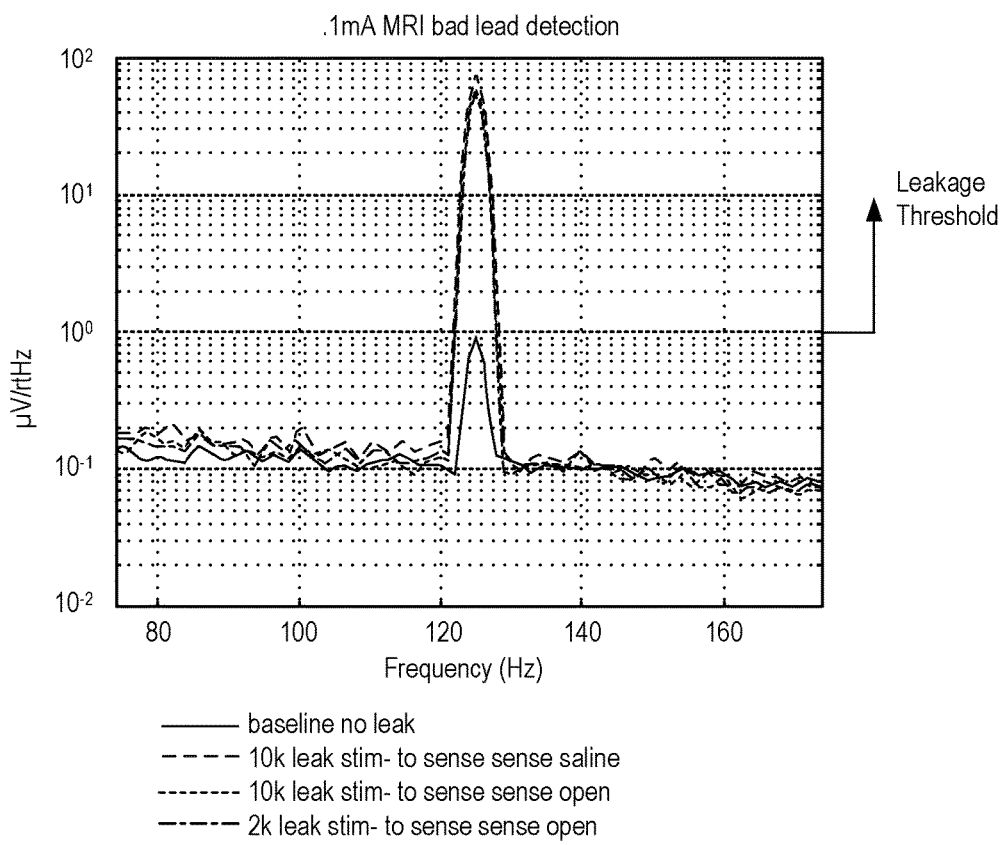
FIG. 6 shows an example of sensed signal amplitudes corresponding to detected leakage and no leakage.

FIG. 6 shows examples of sensed output signals of a differential amplifier of the sensing circuit. The stimulation is being provided from a constant current source producing a 0.1 milli-Amp signal at a typical stimulation frequency of 125 Hz where that amplitude is below the tissue activation threshold so that the sensing is capturing the stimulation signal itself. There is shown a baseline output signal where no leak is present and the output signal has a relatively small peak of just under 1 micro-Volt per root Hertz because of minimal imbalance between the two sensing conduction paths. It will be appreciated that the stimulation signal may be provided during the leakage mode at the same or very similar frequency as stimulation during normal therapy mode, i.e., 125 Hz, so that the impedance of the conduction paths and any leakage is essentially the same in both modes.

The other output signals of FIG. 6 are produced using various different testing parameters where leakage is present between one of the sensing conduction paths and the stimulation path. In one case, there is a leakage path of 10 kilo-ohms in the presence of saline. In another case, there is a leakage path of 10 kilo-ohms in the presence of air. In yet another case, there is a leakage path of 2 kilo-ohms in the presence of air. In all three leakage cases, the sensed output signal produces a peak that is nearly two orders of magnitude greater than the peak of the non-leakage case. Therefore, it is evident that a leakage threshold as discussed above in relation to FIG. 4 may be set at a value greater than 1 micro-Volt per root Hertz, or even greater than 10 micro-Volts per root Hertz, in order to distinguish a leakage case from a non-leakage case. In this example, the leakage threshold may be set as high as 40 micro-Volts per root Hertz and the peaks of the three leakage cases will still exceed the leakage threshold. Therefore, from this example, it can be seen that the leakage threshold may be set within a wide range of 1-40 micro-Volts per root Hertz, depending upon the desired sensitivity to leakage.

While embodiments have been particularly shown and described, it will be understood by those skilled in the art that various other changes in the form and details may be made therein without departing from the spirit and scope of the invention.

What is claimed is:

1. A method of detecting a signal leakage from a conduction path within an implantable medical lead, comprising:
   providing a stimulation signal from a first electrode corresponding to a first conduction path of the implantable medical lead;
   sensing the stimulation signal as a first sensed signal via a second electrode corresponding to a second conduction path of the implantable medical device and sensing the stimulation signal as a second sensed signal via a third electrode corresponding to a third conduction path of the implantable medical lead, with the second and third conduction paths being coupled to a sensing circuit of an implantable medical device; and
   detecting whether there is leakage between the first and second conduction paths and/or between the first and third conduction paths based on the difference in amplitude of the first and second sensed signals.

2. The method of claim 1, wherein detecting whether there is leakage comprises providing the first and second sensed signals to a differential amplifier that produces a sensed output signal.

3. The method of claim 2, wherein detecting whether there is leakage comprises detecting whether an amplitude of the sensed output signal exceeds a leakage threshold, and when the amplitude exceeds the leakage threshold then providing an indication that there is leakage.

4. The method of claim 3, wherein the leakage threshold is greater than 1 microvolt per root Hertz at an amplitude of the stimulation signal of at least 0.1 milliamps.

5. The method of claim 1, wherein providing the stimulation signal comprises providing the stimulation signal with an amplitude that is below a tissue activation threshold.

6. The method of claim 1, further comprising:
   providing a second stimulation signal from the second electrode;
   sensing the second stimulation signal as a third sensed signal via the first electrode corresponding to the first conduction path of the implantable medical device and sensing the second stimulation signal as a fourth sensed signal via the third electrode corresponding to the third conduction path of the implantable medical lead, with the first and third conduction paths being coupled to the sensing circuit of an implantable medical device; and
   detecting whether there is leakage between the first and second conduction paths and/or between the second and third conduction paths based on the difference in amplitude of the third and fourth sensed signals.

7. The method of claim 1, wherein providing the stimulation signal comprises providing the stimulation signal from a constant current stimulation source.

8. The method of claim 7, wherein providing the stimulation signal comprises providing the stimulation signal with an amplitude less than 0.5 milliamps.

9. The method of claim 1, wherein the implantable medical lead is coupled to an implantable medical device comprising a conductive housing and wherein the conductive housing provides an additional conduction path for the stimulation signal of the first conduction path.

10. The method of claim 1, wherein an implantable lead extension is coupled to the implantable medical lead such that the first, second, and third conduction paths extend through the implantable lead extension.

11. An implantable medical system, comprising:
   an implantable medical device having a stimulation engine, having a sensing circuit and having a controller; and
   at least one implantable medical lead providing first, second, and third conduction paths, wherein the controller is configured to electrically couple the first conduction path to the stimulation engine to provide a stimulation signal onto the first conduction path, to electrically couple the second and third conduction paths to the sensing circuit where the second conduction path provides a first sensed signal and the third conduction path provides a second sensed signal, and to monitor an output of the sensing circuit to detect whether there is leakage between the first and second conduction paths and/or between the first and third conduction paths based on a difference in amplitude of the first and second sensed signals.

12. The implantable medical system of claim 11, wherein the sensing circuit comprises a differential amplifier and wherein the controller detects whether there is leakage by providing the first and second sensed signals to a differential amplifier that produces a sensed output signal.

13. The implantable medical system of claim 12, wherein the controller detects whether there is leakage by detecting whether the difference exceeds a leakage threshold, and when the amplitude exceeds the leakage threshold then the controller generates an indication that there is leakage.

14. The implantable medical system of claim 13, wherein the leakage threshold is greater than 1 microvolt per root Hertz at an amplitude of the stimulation signal of at least 0.1 milliamps.

15. The implantable medical system of claim 11, wherein the stimulation signal has an amplitude that is below a tissue activation threshold.

16. The implantable medical system of claim 11, wherein the controller is further configured to electrically couple the second conduction path to the stimulation engine to provide a second stimulation signal onto the second conduction path, to electrically couple the first and third conduction paths to the sensing circuit to produce third and fourth sensed signals, and to monitor the output of the sensing circuit to detect whether there is leakage between the first and second conduction paths and/or between the second and third conduction paths based on a difference in amplitude of the third and fourth sensed signals.

17. The implantable medical system of claim 11, wherein the stimulation engine comprises a constant current stimulation source that produces the stimulation signal.

18. The implantable medical system of claim 17, wherein the stimulation signal has an amplitude less than 0.5 milliamps.

19. The implantable medical system of claim 11, wherein the implantable medical device comprises a conductive housing and wherein the conductive housing provides an additional conduction path for the stimulation signal of the first conduction path.

20. The implantable medical system of claim 11, further comprising an implantable lead extension that extends the first, second, and third conduction paths between the implantable medical device and the implantable medical lead.

21. An implantable medical device, comprising:
a stimulation engine;
a sensing circuit;
a first, a second, and a third lead connectors corresponding to first, second, and third conduction paths; and
a controller that is configured to electrically couple the first lead connector to the stimulation engine to provide a stimulation signal onto the first lead connector, to electrically couple the second and third lead connectors to the sensing circuit to produce first and second sensed signals, and to monitor the output of the sensing circuit to detect whether there is leakage between the first and second conduction paths and/or between the first and third conduction paths based on a difference in amplitude of the first and second sensed signals.

22. The implantable medical system of claim 21, wherein the sensing circuit comprises a differential amplifier and wherein the controller detects whether there is leakage by providing the first and second sensed signals to a differential amplifier that produces a sensed output signal.

23. The implantable medical device of claim 22, wherein the controller detects whether there is leakage by detecting whether an amplitude of the sensed signal exceeds a leakage threshold, and when the amplitude exceeds the leakage threshold then the controller generates an indication that there is leakage.

24. The implantable medical device of claim 23, wherein the leakage threshold is greater than 1 microvolt per root Hertz at an amplitude of the stimulation signal of at least 0.1 milliamps.

25. The implantable medical device of claim 21, wherein the stimulation signal has an amplitude that is below a tissue activation threshold.

26. The implantable medical device of claim 21, wherein the controller is further configured to electrically couple the second lead connector to the stimulation engine to provide a second stimulation signal onto the second lead connector, to electrically couple the first and third lead connectors to the sensing circuit to produce third and fourth sensed signals, and to monitor the output of the sensing circuit to detect whether there is leakage between the first and second conduction paths and/or between the second and third conduction paths based on a difference in amplitude of the third and fourth sensed signals.

27. The implantable medical device of claim 21, wherein the stimulation engine comprises a constant current stimulation source that produces the stimulation signal.

28. The implantable medical device of claim 27, wherein the stimulation signal has an amplitude less than 0.5 milliamps.

29. The implantable medical device of claim 21, wherein the implantable medical device comprises a conductive housing and wherein the conductive housing provides an additional conduction path for the stimulation signal of the first lead connector.

* * * * *